US006238892B1

(12) United States Patent
Mercken et al.

(10) Patent No.: US 6,238,892 B1
(45) Date of Patent: May 29, 2001

(54) MONOCLONAL ANTIBODIES DIRECTED AGAINST THE MICROTUBULE-ASSOCIATED PROTEIN TAU

(75) Inventors: Marc Mercken, Somerville, MA (US); Eva-Maria Mandelkow, Hamburg (DE); Marc Vandermeeren, Geel (BE); Eugeen Vanmechelen, Nazareth-Eke (BE); André Van De Voorde, Lokeren (BE)

(73) Assignee: N.V. Innogenetics S.A., Ghent (BE)

(*) Notice: Subject to any disclaimer, the term of this patent is extended or adjusted under 35 U.S.C. 154(b) by 0 days.

(21) Appl. No.: 08/617,987

(22) Filed: Mar. 15, 1996

Related U.S. Application Data

(63) Continuation of application No. 08/108,758, filed as application No. PCT/EP92/02392 on Oct. 17, 1992, now abandoned.

(30) Foreign Application Priority Data

Oct. 25, 1991 (EP) .................................................. 91402871

(51) Int. Cl.⁷ .............................. C12P 21/04; C12N 5/06; C07K 16/00
(52) U.S. Cl. ...................... 435/70.21; 435/326; 435/331; 530/388.1
(58) Field of Search ............................. 530/387.9, 388.1; 435/7.1, 7.21, 7.92, 70.21, 326, 331; 436/518, 547, 548

(56) References Cited

U.S. PATENT DOCUMENTS 5,601,985 * 2/1997 Trojanowski et al. .
5,811,310 * 9/1998 Ghanbari et al. .

OTHER PUBLICATIONS

Mercken et al, "Monoclonal antibodies with selective specificity for Alzheimer Tau are directed against phosphatase-sensitive epitopes", Acta Neuropathol., 84:265–272 (1992).*
Vandermeeren et al., "Detection of τ Proteins in Normal and Alzheimer's Disease Cerebrospinal Fluid with a Sensitive Sandwich Enzyme–Linked Immunosorbent Assay", J. Neurochem., 61(5):1828–1834 (Nov. 1993).*
Goedert et al, "The abnormal phosphorylation of tau at Ser–202 in Alzheimer disease recapitulates phosphorylation during development", Proc. Natl. Acad. Sci. USA, 90:5066–5070, Jun. 1993).*
Biernat et al, "The switch of tau protein to an Alzheimer–like state includes the phosphorylation of two serine–proline motifs upstream of the microtubule binding region", EMBO J., 11(4):1593–1597, 1992.*

Ksiezak–Reding et al, "Alz 50, a Monoclonal Antibody to Alzheimer's Disease Antigen, Cross–reacts with τ Proteins from Bovine and Normal Human Brain", J. Biol. Chem., 263(17):7943–7947 (Jun. 15, 1988).*
Dickson et al, "A monoclonal antibody that recognizes a phosphorylated epitope in Alzheimer neurofibrillary tangles, neurofilaments and tau proteins immunostains granulovacuolar degeneration", Acta Neuropathol., 73:254–258 (1987).*
Binder et al, "The Distribution of Tau in the Mammalian Central Nervous System", J. Cell Biol., 101:1371–1378 (Oct. 1985).*
Kosik et al, "Epitopes That Span the Tau Molecule Are Shared with Paired Helical Filaments", Neuron, 1:817–825 (Nov. 1988).*
Lee et al, "Identification of an abnormal phosphorylation site in Alzheimer's disease paired helical filaments using synthetic peptides", Proceedings of the American Peptide Symposium, pp. 109–112 (1991).*
Gache et al., "Protein TAU Variants Present in Paired Helical Filaments (PHFs) of Alzheimer Brains", FEBS Letters, 272:65–68 (1990).
Ksiezak–Reding et al., "Alzheimer Disease Proteins (A68) Share Epitopes with Tau but Show Distinct Biochemical Properties", J. Neuroscience Res., 25:420–430 (1990).
Lee et al., "A68: A Major Subunit of Paired Helical Filaments and Derivatized Forms of Normal Tau", Science, 251:675–678 (1991).
Lindwall and Cole, "The Purification of Tau Protein and the Occurrence of Two Phosphorylation States of Tau in Brain", JBC, 259:12241 (1984) No month is listed in the published article.
Ghanbari et al., "Detection and Measurement of Alzheimer's Disease Asociated Protein (DAP) in Cerebrospinal Fluid (CSF): An Antemortem Marker for Alzheimer's Disease", Abstract (1991) (no month available on reference).
Lichtenberg–Kraag et al., "Phosphorylation–dependent Epitopes of Neurofilament Antibodies on Tau Protein and Relationship with Alzheimer Tau", Proc. Nat'l. Acad. Sci. USA, 89:5384–5388 (Jun. 1992).
Goedert et al, PNAS 90:5066–5070, Jun. 1993.*

* cited by examiner

Primary Examiner—Patricia A. Duffy
(74) Attorney, Agent, or Firm—Merchant & Gould P.C.

(57) ABSTRACT

A monoclonal antibody which forms an immunological complex with a phosphorylated epitope of an antigen belonging to human abnormally phosphorylated tau protein. The tau protein ca be obtained from a brain homogenate, itself isolated from the cerebral cortex of a patient having Alzheimer's disease.

3 Claims, 7 Drawing Sheets

FIG. 4

12345678    12345678

■ ■

134         AT8

SEQUENCE LISTING

```
<160> NUMBER OF SEQ ID NOS:  4

<210> SEQ ID NO 1
<211> LENGTH: 9
<212> TYPE: PRT
<213> ORGANISM: Homo sapiens
<220> FEATURE:
<221> NAME/KEY: MOD_RES
<222> LOCATION: (3)
<223> OTHER INFORMATION: Note = "S is phosphorylated"
<221> NAME/KEY: MOD_RES
<222> LOCATION: (6)
<223> OTHER INFORMATION: Note = "S is phosphorylated"

<400> SEQUENCE: 1

Tyr Ser Ser Pro Gly Ser Pro Gly Thr
  1               5

<210> SEQ ID NO 2
<211> LENGTH: 9
<212> TYPE: PRT
<213> ORGANISM: Homo sapiens
<220> FEATURE:
<221> NAME/KEY: MOD_RES
<222> LOCATION: (6)
<223> OTHER INFORMATION: Note = "S is phosphorylated"

<400> SEQUENCE: 2

Tyr Ser Ser Pro Gly Ser Pro Gly Thr
  1               5

<210> SEQ ID NO 3
<211> LENGTH: 9
```

```
<212> TYPE: PRT
<213> ORGANISM: Homo sapiens
<220> FEATURE:
<221> NAME/KEY: MOD_RES
<222> LOCATION: (1)
<223> OTHER INFORMATION: Note = "X is any amino acid, X is absent or
      present"
<221> NAME/KEY: MOD_RES
<222> LOCATION: (2)
<223> OTHER INFORMATION: Note = "X is any amino acid, X is absent or
      present"
<221> NAME/KEY: MOD_RES
<222> LOCATION: (3)
<223> OTHER INFORMATION: Note = "S is phosphorylated"
<221> NAME/KEY: MOD_RES
<222> LOCATION: (5)
<223> OTHER INFORMATION: Note = "X is any amino acid"
<221> NAME/KEY: MOD_RES
<222> LOCATION: (6)
<223> OTHER INFORMATION: Note = "S is phosphorylated"
<221> NAME/KEY: MOD_RES
<222> LOCATION: (8)
<223> OTHER INFORMATION: Note = "X is any amino acid, X is absent or
      present
<221> NAME/KEY: MOD_RES
<222> LOCATION: (9)
<223> OTHER INFORMATION: Note = "X is any amino acid, X is absent or
      present"

<400> SEQUENCE: 3

Xaa Xaa Ser Pro Xaa Ser Pro Xaa Xaa
 1               5

<210> SEQ ID NO 4
<211> LENGTH: 9
<212> TYPE: PRT
<213> ORGANISM: Homo sapiens
<220> FEATURE:
<221> NAME/KEY: MOD_RES
<222> LOCATION: (1)
<223> OTHER INFORMATION: Note = "X is any amino acid, X is absent or
      present"
<221> NAME/KEY: MOD_RES
<222> LOCATION: (2)
<223> OTHER INFORMATION: Note = "X is any amino acid, X is present or
      absent"
<221> NAME/KEY: MOD_RES
<222> LOCATION: (5)
<223> OTHER INFORMATION: Note = "X is any amino acid"
<221> NAME/KEY: MOD_RES
<222> LOCATION: (6)
<223> OTHER INFORMATION: Note = "S is phosphorylated"
<221> NAME/KEY: MOD_RES
<222> LOCATION: (8)
<223> OTHER INFORMATION: Note = "X is any amino acid, X is absent or
      present"
<221> NAME/KEY: MOD_RES
<222> LOCATION: (9)
<223> OTHER INFORMATION: Note = "X is any amino acid, X is absent or
      present"

<400> SEQUENCE: 4

Xaa Xaa Ser Pro Xaa Ser Pro Xaa Xaa
 1               5
```

MONOCLONAL ANTIBODIES DIRECTED AGAINST THE MICROTUBULE-ASSOCIATED PROTEIN TAU

Figure 1:
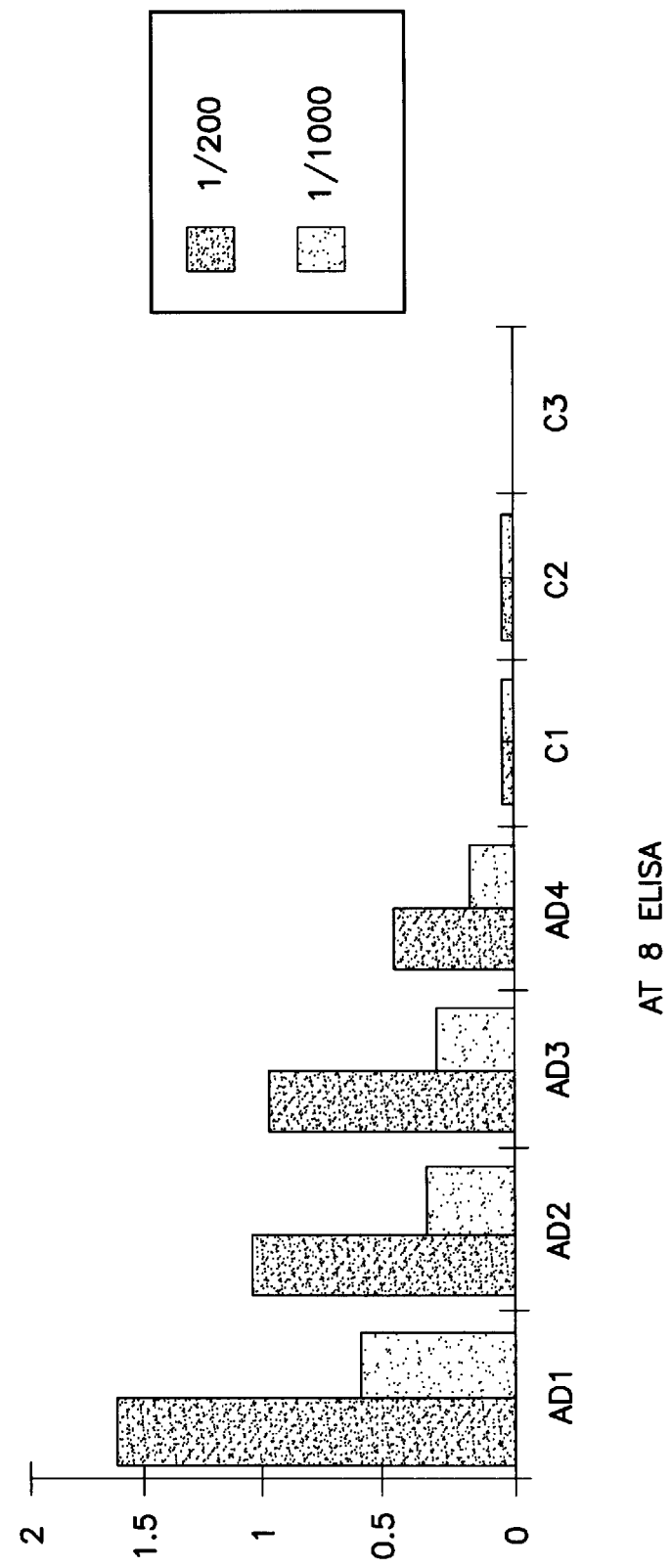

This is a continuation of application Ser. No. 08/108,758, filed Sep. 2, 1993, now abandoned, which is a 371 of PCT/EP92/02392 filed Oct. 17, 1992.

The invention relates to new monoclonal antibodies directed against a particular epitope present on the human microtubule-associated protein tau, to the hybridoma secreting these monoclonal antibodies, to the process for diagnosing brain diseases involving the particular epitope of the tau protein, and to the monoclonal antibodies recognizing said epitope.

Tau is a microtubule-associated protein which is synthesized in the neurons (Kosik, K. S. et al., 1989) of several species, including humans and which is abundantly present in the axonal compartment of these neurons (Binder, L. I. et al., 1985). Functionally the tau protein is involved in the polymerization of tubulin (Weingarten, M. D. et al., 1975) and presumably in reducing microtubule instability (Bre, M. H. and Karsenti, E. 1990).

Tau protein is also the major constituent of paired helical filaments (PHF), characteristic structures found as neurofibrillary tangles in tissue sections of the brain of Alzheimer patients (Greenberg, S. and Davies, P., 1990; Lee, V. M.-Y. et al., 1991). The protein exists as a family of different isoforms of which 4 to 6 isoforms are found in normal adult brain but only 1 isoform is detected in fetal brain (Goedert, M. et al., 1989). The diversity of the isoforms is generated from a single gene by alternative mRNA splicing (Himmler, A., 1989). The most striking feature of tau protein as predicted from molecular cloning is a stretch of 31 or 32 amino acids occurring in the carboxy-terminal part of the molecule that is repeated 3 or 4 times. Additional diversity is generated through 29 or 58 amino acid long insertions in the $NH_2$-terminal part of the molecules (Goedert, M. et al., 1989).

Tau variants of 64 and 69 kDa, which are abnormally phosphorylated as revealed by the decrease in their molecular mass observed after alkaline phosphatase treatment, have been detected exclusively in brain areas showing neurofibrillary tangles and senile plaques (Flament, S. et al., 1989 and 1990). The sites of phosphorylation by 4 different kinases have been mapped in the C-terminal microtubule-binding half of tau and it could be shown that the action of a calcium calmodulin-dependent kinase on bacterially expressed tau resulted in a phosphorylation of Ser(405) which induced a lower electrophoretical mobility (Steiner, B. et al., 1990).

Several antibodies are reported that show reactivity to human tau either because they are directed to nonspecific phosphorylated epitopes present on neurofilament and subsequently shown to cross-react with normal and abnormally phosphorylated tau (Nukina, N. et al., 1987; Ksiezak-Reding et al., 1987) or because they recognized specific epitopes on normal and abnormally phosphorylated tau.

The Alz50 monoclonal antibody (Wolozin, B. L. et al., 1986; Nukina et al., 1988) recognizing a phosphate-independent epitope present on tau variants of bovine origin and of normal and abnormally phosphorylated tau from human origin (Ksiezak-Reding, H. et al., 1988, Flament, S. and Delacourte, A. 1990) belongs to the latter class of antibodies. The epitope recognized by this monoclonal is specifically expressed in the somatodendritic domain of degenerating cortical neurons during Alzheimer disease (Delacourte, A. et al., 1990).

The Alz50 epitope has recently been mapped to the $NH_2$-terminal part of the tau molecule (Ksiezak-Reding, H. et al., 1990; Goedert, M. et al., 1991). Due to its cross-reactivity with normal tau, this antibody is only able to discriminate normal from abnormally phosphorylated tau by the use of Western blotting detection of brain homogenates or by ammonium sulfate-concentrated CSF, or else by using a sandwich immunoassay on brain homogenates (Ghanbari et al., 1990; Wolozin, B. and Davies, P. 1987; European patent publication ("EP") 444 856). A CSF-based assay using antibodies directed against PHF was first described by Mehta et al., 1985, but shows considerable overlap between Alzheimer CSF and CSF from controls. The epitope recognized by this antibody was identified as part of ubiquitin (Perry et al., 1989).

Other monoclonal antibodies have been developed to recognize tau protein. For instance, monoclonal antibody 5E2 was raised by immunization with human fetal heat-stable microtubule-associated proteins and recognizes an epitope spanning amino acids 156–175 which is present in normal and abnormally phosphorylated tau (Kosik, K. S. et al., 1988).

Other antibodies such as tau 1 and several others were raised by immunization with bovine tau, bovine heat-stable microtubule-associated protein, or rat brain extracts (Binder, L. I. et al., 1985; Kosik, K. S. et al., 1988), and most of the antibodies recognize the normal and the abnormally phosphorylated tau (Ksiezak-Reding, R. et al., 1990).

An antibody named "423", raised against the core of PHF, reacted specifically with a 9.5 and 12-kDa fragment of the tau protein, localized in the repetitive elements of tau, but recognized neither normal human tau nor the abnormally phosphorylated tau in Alzheimer's brain (Wischik, C. H. et al., 1988).

This antibody has been used to discriminate Alzheimer PHF pathology from normal controls in brain homogenates (Harrington, G. R. et al., 1990; patent WO89/03993).

Thus far, none of all the antibodies described heretofore has had an absolute specificity for the abnormally phosphorylated tau either by immunohistology, Western blotting, or ELISA. Quantitative measurements of normal and abnormally phosphorylated tau have until now only been able to detect tau in brain homogenates, in brain extracts containing PHF, or in concentrated CSF samples after Western blotting (Ghanbari H. A. et al., 1990; Harrington C. R. et al., 1990, Wisniewski, H. M. et al., 1989; Wolozin, B. and Davies, P. 1987).

The aim of the present invention is therefore to provide monoclonal antibodies which are specifically able to detect only abnormally phosphorylated tau present in brain tissue sections, in brain extracts, or in body fluids such as cerebrospinal fluid.

The invention also provides the hybridoma secreting such monoclonal antibodies.

The invention further provides the epitope of tau protein which is expressed in abnormally phosphorylated tau in brain tissue sections or in brain homogenates or in body fluids, such as cerebrospinal fluid, and which is recognized by such monoclonal antibodies.

The invention still further provides the epitope of tau protein expressed in the brain of patients affected with neurological disorders such as Alzheimer's disease and Down syndrome.

The invention yet further provides a process for the detection or diagnosis in vitro of brain diseases involving tau protein.

The monoclonal antibodies of the invention are characterized by the fact that they react with an epitope which is present in abnormally phosphorylated human tau. The monoclonal antibodies are furthermore characterized by the fact that they form an immunological complex with abnormally phosphorylated human tau, and more specifically with a non-structural epitope present in abnormally phosphorylated human tau.

By "non-structural" epitopes is meant epitopes which depend for their antibody recognition both on their primary structure as well as on post-translational modifications and conformation in such a way that particular treatments (e.g. formalin fixation, detergent treatment, dephosphorylation) may alter or destroy the epitopes.

The expression "form an immunologically complex with" means that a monoclonal antibody of the invention binds to the aforementioned antigen under the conditions used in any one of the following techniques:

Light immunomicroscopy:

Brain tissue samples, obtained at surgery or autopsy, are fixed by immersion in 4% formalin or Bouin's fixative and embedded in paraffin. Four-mm-thick sections are prepared. The monoclonal antibodies of the invention are applied in conjunction with a technique to visualize the formed immune complexes such as the avidin-biotinylated peroxidase complex technique (Hsu, S. M., et al., 1981) using 3,3'-diaminobenzidine tetrahydrochloride for development of color. Sections are counterstained with Harris haematoxylin stain.

Immunoelectron microscopy in tissue sections:

Brain tissue sample, obtained at surgery or autopsy, is fixed in either Bouin's fixative or 10% buffered formalin before sectioning 60 mm thick without embedding (Vibratome). The monoclonal antibody of the invention is used for immunostaining by the indirect immunogold method after which the sections are fixed, embedded and sectioned for electron microscopy, all following standard protocols known to those skilled in the art (Brion, J. P. et al., 1985).

Immunoblotting procedures:

For immunoblotting, fractions enriched in PHF are prepared as described by Iqbal, K. et al. (1984) or Greenberg, S. and Davies, P. (1990). For the second method, postmortem tissue is used, consisting mostly of gray matter from the frontal and temporal cortex, which is obtained from histologically confirmed Alzheimer patients. This Alzheimer gray matter brain sample (5–10 g) is homogenized with 10 vol. of cold buffer H (10 mM Tris/1 mM EGTA/0.8 M NaCl/10% sucrose, pH 7.4) in a Teflon/glass Potter S (Braun, Germany) homogenizer. After centrifugation in a 60 Ti MSE rotor at 27000×g for 20 min at 4° C., the pellet is removed and the supernatant is adjusted to 1% (wt/vol) N-laurosylsarcosine and 1% (vol/vol) 2-mercaptoethanol and incubated while rotating on a mixer 820 (Swelab, Sweden) for 2.5 hours at 37° C. The supernatant mixture is centrifuged at 108,000×g for 35 min at 20° C. The PHF-tau-containing pellet is gently washed with PBS and finally suspended in 1 ml of the same buffer.

SDS-polyacrylamide electrophoresis is performed under reducing conditions on 12% gels (Laemmli U. K., 1970). After electrophoresis, the proteins are either fixed and stained with Coomassie brilliant blue, or transferred (Towbin H. et al., 1979) to nitrocellulose sheets (Hybond-C, Amersham) or Immobilon filters (Millipore).

After transfer the filters are presoaked in PBS containing 0.05% (v/v) Tween 20 (Tween-PBS) and then incubated for 1 h in Tween-PBS containing 5% (w/v) skimmed dried milk and 10% (v/v) newborn calf serum (blocking buffer). Next, the filters are treated overnight at 4° C. with a monoclonal antibody of the invention appropriately diluted in blocking buffer.

The filters are then washed three times in Tween-PBS and treated for 1.5 h at room temperature with horseradish peroxidase-labeled rabbit anti-mouse IgG (Dakopatts, Denmark) diluted 1/3000 in blocking buffer. After three washes in Tween-PBS, streptavidine-biotinylated horseradish peroxidase complex (Amersham) diluted 1/250 in blocking buffer is applied for 1.5 h at room temperature. Thereafter, the filters are washed three times in Tween-PBS and once in PBS. The filters are then incubated in PBS containing 0.05% (w/v) diaminobenzidine and 0.03% (v/v) hydrogen peroxide until background staining develops.

It should be clear that the formation of an immunological complex between the monoclonal antibodies and the antigen is not limited to the precise conditions described above, but that all techniques that respect the immunochemical properties of the antibody and antigen binding will produce similar formation of an immunological complex.

Human abnormally phosphorylated tau is a class of at least two tau proteins of 64 and 68 kDa (Flament, S. et al., 1989 and Delacourte, A. et al., 1990) which are specifically expressed in the somatodendritic domain of the degenerating cortical neurons during Alzheimer's disease and of which the lower electrophoretic mobility can be attributed to abnormal phosphorylation. Although kinase activities have been described that can provoke an additional phosphorylation of normal tau with the concomitant shift in electrophoretic mobility, none of these phosphorylations can induce the formation of the epitope of the invention (Ishiguro, K. et al., 1988; Steiner, B. et al., 1990).

According to an advantageous embodiment of the invention, the monoclonal antibody forms an immunological complex with a phosphorylated epitope of an antigen belonging to human abnormally phosphorylated tau protein, with said tau protein being liable to be obtained from a brain homogenate, itself isolated from the cerebral cortex obtained from a patient having Alzheimer's disease or having died from Alzheimer's disease.

The expression "phosphorylated epitope" means an epitope that is destroyed when it is treated with a phosphatase enzyme, such as alkaline phosphatase. In the phosphorylated epitope, the serines are in the form of phosphoserines.

A "brain homogenate" and abnormally phosphorylated tau protein can be obtained by one skilled in the art according to standard methods such as the method of Iqbal, K. et al. (1984) or the method of Greenberg, P. G. and Davies, P. (1990).

Monoclonal antibodies of the invention are characterized by the fact that they form an immunological complex either with the peptide YSSPGSPGT or YSSPGSPGT (SEQ ID NO:2), preferably YSSPGAPGT (SEQ ID NO:1), phosphorylated at the positions marked with * or with any other peptide capable of forming an immunological complex with a monoclonal antibody, which itself is liable to form a complex with the above-mentioned peptide.

The peptide YSSPGSPGT or YSSPGSPGT (SEQ ID NO:2), preferably YSSPGSPGT (SEQ ID NO:1), will be hereinafter designated as "the epitope" of the invention. The serines in positions 199 and 202 using the numbering of human tau 40 (Goedert, M. et al., 1989) are in the form of phosphoserines. The epitope spans the amino acids 197–205 using the above-mentioned numbering.

The peptides capable of forming an immunological complex with a monoclonal antibody, which itself is liable to form a complex with the above-mentioned peptide, will be defined as the "variant peptides".

A peptide phosphorylated at a certain position means that the serine is in the phosphoserine form.

The invention also relates to monoclonal antibodies which are not liable to form an immunological complex with normal tau protein.

The monoclonal antibodies of the invention are not able to form an immunological complex with tau protein present in brain homogenates derived from human brain, isolated from a patient who died of non-neurological disorders.

The monoclonal antibodies of the invention also are not capable of forming an immunological complex with the above-defined epitope previously treated with a dephosphorylating agent such as alkaline phosphatase.

The monoclonal antibodies of the invention are further not capable of forming an immunological complex with any variant peptide above-defined and previously treated with a dephosphorylating agent.

Advantageously, the monoclonal antibodies of the invention are characterized by:

the fact that they form an immunological complex with the abnormally phosphorylated forms of tau protein, present in homogenates of human brain obtained from a patient who died of Alzheimer's disease and the fact that these abnormally phosphorylated tau proteins present an apparent molecular weight which is higher than that of normal tau proteins, derived from brain homogenate, isolated from a patient who died of non-neurological disorders and the fact that the apparent molecular weight of such abnormally phosphorylated tau proteins can be decreased to that of normal tau proteins by treatment of such abnormally phosphorylated tau proteins with a dephosphorylating agent.

The invention also relates to monoclonal antibodies which form an immunological complex with the abnormally phosphorylated 64 and 68 kDa forms of tau protein present in brain homogenate as defined above.

A preferred monoclonal antibody of the invention is secreted by the hybridoma deposited at ECACC (European Collection of Animal Cell Cultures, Vaccine Research and Production Laboratory, Public Health and Laboratory Service (PHLS), Centre for Applied Microbiology and Research, Porton Down, GB-Salisbury, Wiltshire SP4 OJG) on Oct. 8, 1991 under No. 91100806. This hybridoma will be hereinafter referred as "hybridoma AT8", and the secreted monoclonal antibody will be referred as "monoclonal antibody AT8".

The invention also relates to an hybridoma which secretes a monoclonal antibody according to the invention, and particularly the hybridoma filed at ECACC on Oct. 8, 1991 under No. 91100806.

The monoclonal antibodies of this invention are obtained by a process involving obtention and isolation of hybridomas which secrete the monoclonal antibodies.

A process for obtaining such a hybridoma involves:

starting from spleen cells of an animal, e.g. mouse or rat, previously immunized in vivo or from spleen cells of such animals previously immunized in vitro with an antigen recognized by the monoclonal antibodies of the invention, such as the monoclonal antibody secreted by the hybridoma deposited at ECACC on Oct. 8, 1991 under No. 91100806;

fusing such immunized cells with myeloma cells under hybridoma-forming conditions; and selecting those hybridomas which secrete the monoclonal antibodies which specifically recognize an epitope of the above-said antigen and which form an immunological complex with the abnormally phosphorylated form of tau protein or with the phosphorylated peptide comprising the epitope of tau protein.

A process for producing the corresponding monoclonal antibodies involves:

culturing the selected hybridoma as indicated above in an appropriate culture medium; and recovering the monoclonal antibodies excreted by the selected hybridoma, or alternatively implanting the selected hybridoma into the peritoneum of a mouse and, when ascites have been produced in the animal, recovering the monoclonal antibodies then formed from such ascites.

The monoclonal antibodies of the invention can be prepared by conventional in vitro techniques such as the culturing of immobilized cells using, e.g., hollow fibers or microcapsules or the culturing of cells in homogeneous suspension using, e.g., airlift reactors or stirred bioreactors.

The invention also relates to a peptide (antigen), which can be obtained from a brain homogenate, itself isolated from the cerebral cortex obtained from a patient having Alzheimer's disease, and which forms an immunological complex with the monoclonal antibody of the invention.

The invention further relates to peptides (antigens) which are liable to form an immunological complex with any one of the monoclonal antibodies of the invention and which contain or are constituted by the sequence YSSPGSPGT (SEQ ID NO:1), or YSSPGSPGT (SEQ ID NO:1), phosphorylated at the positions marked with *, or which contain or are constituted by the sequence of the variant peptides defined above, i.e., the peptides able to form an immunological complex with a monoclonal antibody, which itself is liable to form a complex with the peptide YSSPGSPGT (SEQ ID NO:1) or YSSPGSPGT (SEQ ID NO:1).

The invention also relates to peptides (antigens) of about 100 amino acids which contain the sequence YSSPGSPGT (SEQ ID NO:1) or YSSPGSPGT (SEQ ID NO:1), phosphorylated at the positions marked with *, or which contain the sequence of the variant peptides defined above.

The invention also relates to peptides (antigens) which contain the sequence (SEQ ID NO:2)

$(X_1)_p(X_2)_q SPX_3 SP(X_4)_r(X_5)_s$ or (SEQ ID NO:3)

$(X_1)_p(X_2)_q SPX_3 SP(X_4)_r(X_5)_s$ (SEQ ID NO:4), preferably $(X_1)_p(X_2)_p SPX_3 SP(X_4)_r(X_5)_s$ (SEQ ID NO:4), in which $X_1$, $X_2$, $X_3$, $X_4$, $X_5$ are any one of the 20 amino acids and p, q, r, s are 0 or 1, phosphorylated at places marked by *, provided that such peptides are able to form an immunological complex with the monoclonal antibodies of the invention.

The invention also relates to the above-mentioned peptides which are liable to generate monoclonal antibodies of the invention.

The invention also relates to a peptide (antigen) which is contained in the brain, in the cerebrospinal fluid, or in the serum of a patient having Alzheimer's disease or any brain disease involving PHF or tau protein and which forms an immunological complex with a monoclonal antibody of the invention.

A method for preparing the peptides of the invention preferably involves: starting from the C-terminal amino acid, the successive aminoacyls in the requisite order, or aminoacyls and fragments formed beforehand and already containing several aminoacyl residues in the appropriate order,. or alternatively several fragments prepared in this manner beforehand, are coupled successively in pairs, care being taken to protect all the reactive groups carried by these aminoacyls or fragments except for the amine groups of one and the carboxyl group of the other, which must normally participate in peptide bond formation, in particular after activation of the carboxyl group, according to methods known in peptide synthesis, and so on, proceeding stepwise up to the N-terminal amino acid.

In this process, it is possible to use previously phosphorylated amino acids (De Bont H. B. A. et al., 1990) or it is possible to carry out the phosphorylation after the synthesis of a non-phosphorylated sequence, as explained hereafter.

The invention is also related to a process for the preparation of the antigen according to the invention, starting from said antigen in non-phosphorylated form which comprises:

reacting said antigen, which is non-phosphorylated, with a kinase enzyme capable of recognizing the non-phosphorylated epitope of the antigen and of modifying the epitope to a phosphorylated epitope recognized by the monoclonal antibodies of the invention.

The kinase used is advantageously extracted from brain according to methods known to those skilled in the art (Ishiguro K. et al., 1988; Baudier, J. and Cole, R. D., 1987; Vallee, R. B., 1980) and is different from the kinases referred to in Steiner et al. (1990).

The non-phosphorylated antigen is, for instance, a normal human tau protein which, by phosphorylation with the above-mentioned kinase, gives rise to an abnormally phosphorylated tau protein, which is recognized by the monoclonal antibody of the invention. Such abnormally phosphorylated tau protein is new.

The antigen of the invention, which can be prepared by methods known to those skilled in the art (Igbal, K. et al., 1984; Greenberg S. G. and Davies, P., 1990) from the cerebral cortex obtained from a patient having Alzheimer's disease or having died of Alzheimer's disease, is characterized by its ability to form an immunological complex with the monoclonal antibody of the invention, particularly with the monoclonal antibody secreted by the hybridoma deposited at the ECACC under No. 91100806.

The antigen of the invention is advantageously contained in the brain, in the cerebrospinal fluid or the serum of a patient having Alzheimer's disease, Down syndrome, Pick's disease, SSPE or other neurological diseases in which the occurrence of PHF and abnormally phosphorylated tau protein is implicated; this antigen provokes an immunological reaction with the monoclonal antibody of the invention.

The invention also relates to a process for the detection or the diagnosis in vitro of brain disease involving PHF and tau protein, i.e. Alzheimer's disease, which involves:

bringing one of the monoclonal antibodies of the invention into contact with a preparation of PHF isolated from a patient having Alzheimer's disease, or preferably from a diseased patient having had Alzheimer's disease under conditions suitable for producing an antigen-antibody complex;

separating the antigen from said complex and recovering the antigen sought in a purified form.

The preparation of PHF can be carried out according to Iqbal K. et al. (1984) or Greenberg et al. (1990).

Advantageously, the monoclonal antibody used is in an immobilized state on a suitable support such as a resin. The process for the detection of the antigen can then be carried out as follows:

bringing the supernatant containing proteins and polypeptides, extracted from brain tissues in a known manner (Iqbal, K. et al., 1989; Greenberg S. S. and Davies, P., 1990), into contact with the monoclonal antibody under conditions that allow the formation of an immunological complex;

washing the immobilized antibody-antigen complex so formed;

treating that complex with a solution (e.g., 3 M potassium thiocyanate, 2.5 M magnesium chloride, 0.2 M citrate-citric acid, pH 3.5 or 0.1 M acetic acid) capable of producing the dissociation of the antigen-antibody complex; and recovering the antigen in a purified form.

The process of the invention for the detection or diagnosis in vitro of brain disease involving tau protein and PHF, e.g., Alzheimer's disease, includes:

bringing a sample of a brain homogenate, or of cerebrospinal fluid, or of serum from a patient suspected of suffering of brain disease involving tau protein and PHF, more particularly Alzheimer's disease, into contact under in vitro conditions with the monoclonal antibody of the invention under conditions suitable for producing an antigen-antibody complex; and detecting the immunological binding of said antibody to said sample of brain homogenate, or of cerebrospinal fluid, or of serum.

The detection of the immunologically bound monoclonal antibody can be achieved in a conventional manner. Advantageously, the monoclonal antibody of the invention itself carries a marker or a group for direct or indirect coupling with a marker as exemplified hereinafter. Also, a polyclonal antiserum can be used which was raised by injecting the antigen of the invention in an animal, preferably a rabbit, and recovering the antiserum by immunoaffinity purification in which the polyclonal antibody is passed over a column to which the antigen is bound and eluting the polyclonal antibody in a conventional manner. Detection can also be achieved by competition binding of the antigen with a labeled peptide comprising the epitope of the invention.

A particularly advantageous embodiment of the process of the invention comprises contacting a sample of cerebrospinal fluid (containing the corresponding antigen) obtained from a patient to be diagnosed with the monoclonal antibody of the invention.

The invention also relates to a kit for the diagnosis in vitro of one of the following diseases: Alzheimer's disease, Down's syndrome, Pick's disease, SSPE and other neurological disorders in which abnormally phosphorylated tau protein or paired helical filaments are implicated. Such a kit would contain:

at least a microplate for deposition thereon of any monoclonal antibody of the invention;

a preparation containing the sample to be diagnosed in vitro, possibly together with a labeled peptide containing the epitope of the invention and preferably with the peptide YSSPGSPGT (SEQ ID NO:1) or YSSPGSPGT (SEQ ID NO:2) phosphorylated at the positions marked with *;

a second antibody which can be a monoclonal antibody recognizing an epitope of normal tau, or of abnormally phosphorylated tau protein, or of any peptide of the invention, such epitope being different from the one of the invention, or which can be a polyclonal antibody of normal tau or of abnormally phosphorylated tau or of a peptide of the invention, such polyclonal antibody being liable to form an immunological complex with epitopes which are all different from the epitope of the invention, and the polyclonal antibody being preferably purified by immunoaffinity chromatography using immobilized tau protein, or a marker either for specific tagging or coupling with the second antibody;

appropriate buffer solutions for carrying out the immunological reaction between: 1) the monoclonal antibody of the invention and a test sample and 2) the bonded second antibody and the marker.

The labeled peptide mentioned above can be a peptide which has been labeled by any means known to those skilled in the art. Likewise, the marker specific for tagging and coupling can be any marker known to those skilled in the art.

The intention also relates to a kit, as described above, also containing the antigen of the invention, the antigen of the invention being either a standard (for quantitative determination of an antigen which is sought) or a competitor, with respect to an antigen which is sought, whereby the kit can be used in a competition dosage process.

THE FIGURES

FIG. 1: Reactivity of AT8 to brain homogenates of Alzheimer patients or normal controls using the AT8 monoclonal antibodies as binding antibodies and rabbit anti-tau polyclonal antibodies together with horseradish peroxidase-conjugated donkey anti-rabbit antiserum for detection.

$AD_1$–$AD_4$: Brain homogenates from 4 different Alzheimer patients diluted 1/200 (solid bars) or 1/1000 (stippled bars).

$C_1$–$C_4$: Brain homogenates from 4 different controls, diluted 1/200 (solid bars) or 1/1000 (stippled bars).

The ordinate represents the optical density at 450 nm and the abscissa represents the different samples.

Figure 2:
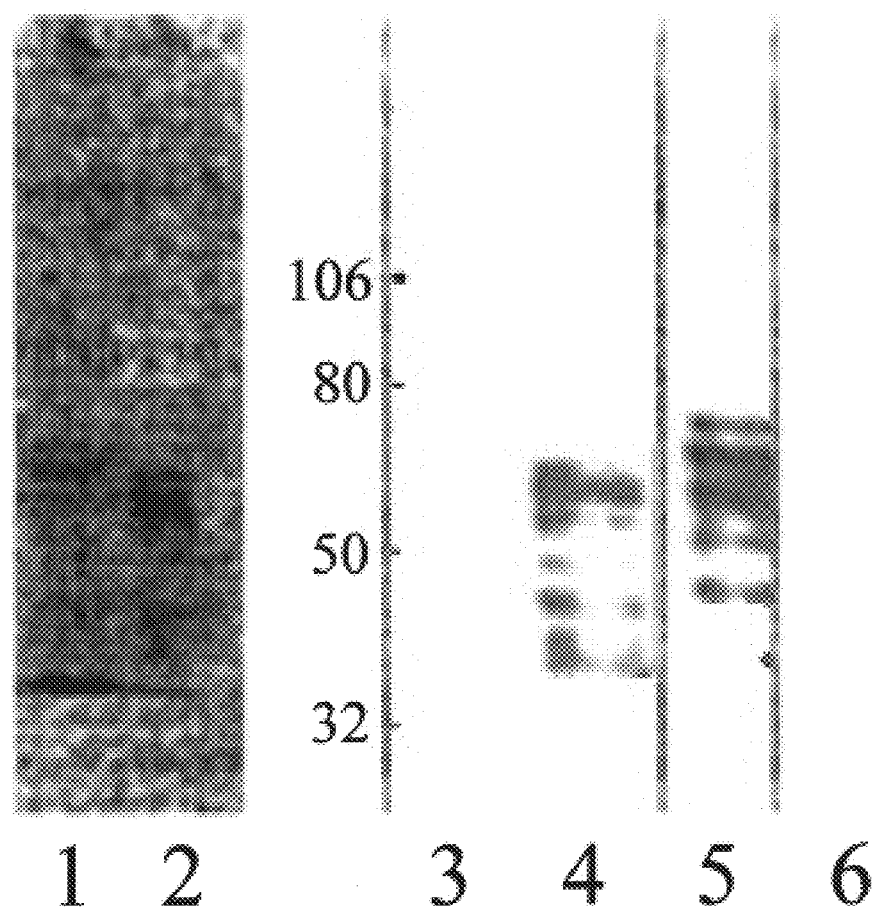

FIG. 2: Western blotting detection of normal tau or PHF-tau using either the monoclonal antibodies Tau-1 or AT8. Lanes 1 and 2: Coomassie Brilliant Blue staining of PHF-tau (lane 1) or normal tau (lane 2). Lanes 3 to 6: Western blotting of PHF-tau (lanes 3 and 5) or normal tau (lanes 4 and 6) using either Tau-1 monoclonal antibodies (lanes 3 and 4) or AT8 monoclonal antibodies (lanes 5 and 6).

FIGS. 3A, 3B, 3C and 3D:

Detection of tau protein by immunochemistry.

Figure 3A:

FIG. 3A: Section from hippocampus of a patient with Alzheimer's disease. Magnification 78×.

Figure 3B:

FIG. 3B: Section from hippocampus of an aged control patient deceased from non-neurological causes. Magnification 78×.

Figure 3C:
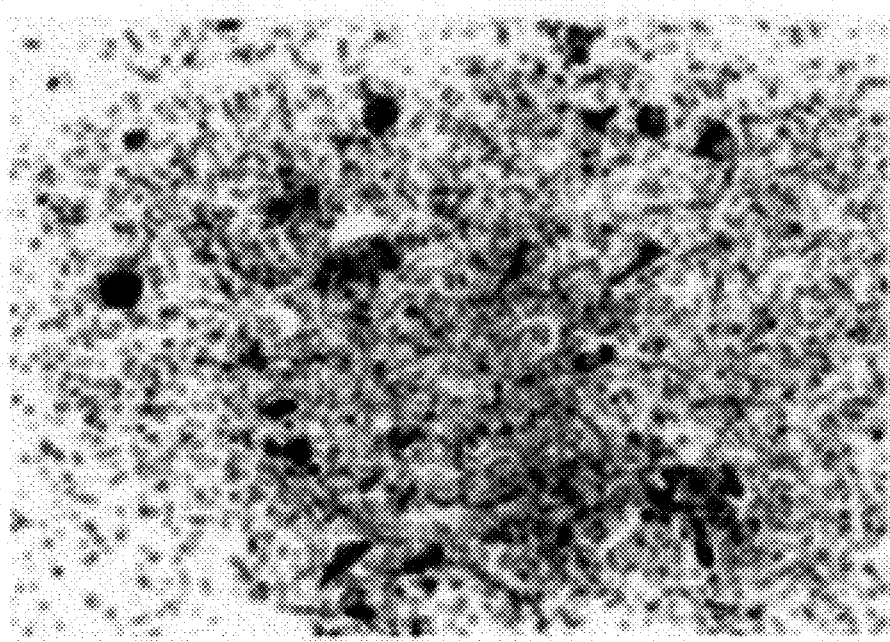

FIG. 3C: Section from hippocampus of a patient with Alzheimer's disease. Magnification 245×.

Figure 3D:

FIG. 3D: Section from hippocampus of an aged control patient deceased from non-neurological causes. Magnification 245×.

Figure 4:
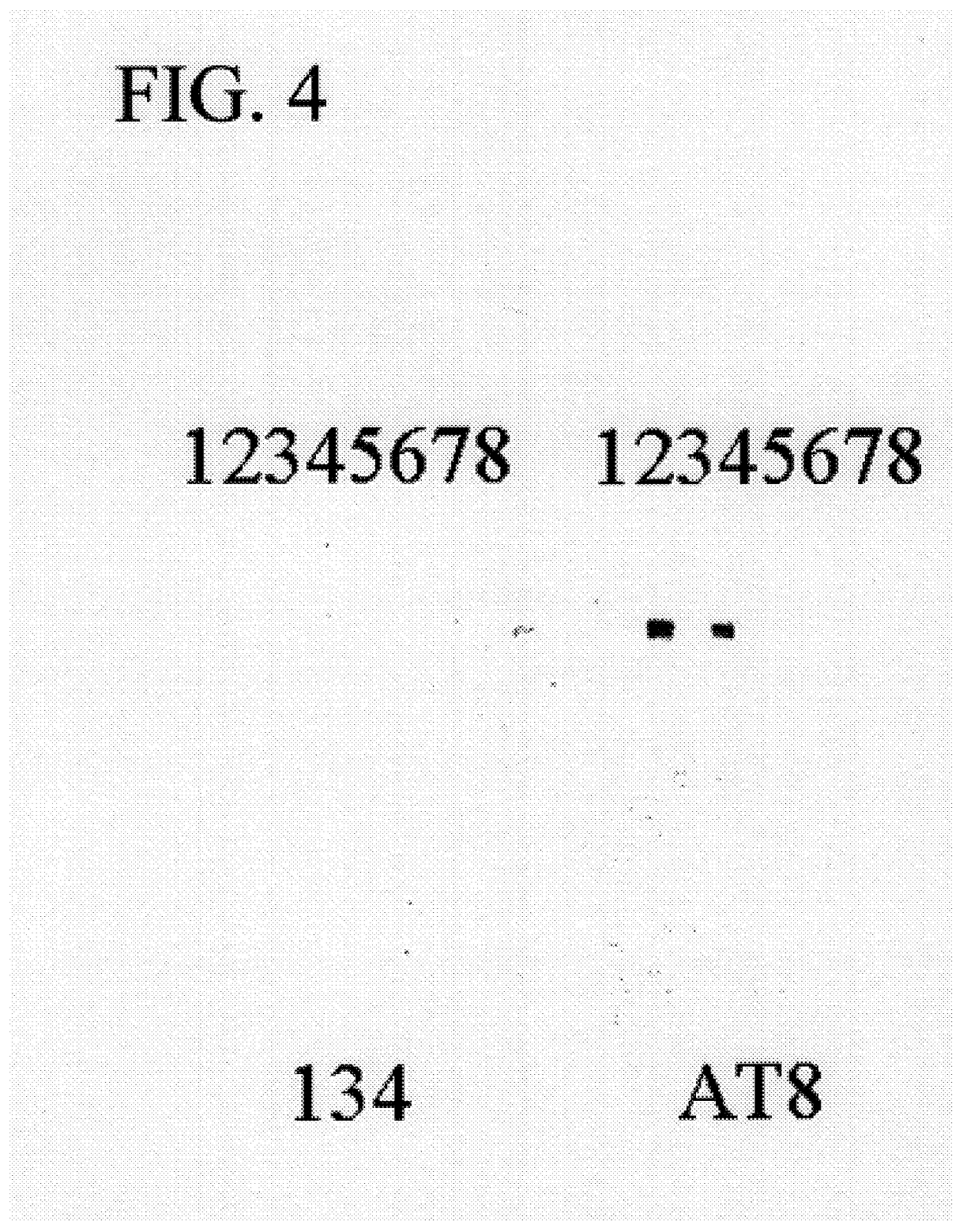

FIG. 4: Immunoblot analysis of Example 5 of a mutated recombinant tau (clone htau24) phophorylated with the protein kinase activity from rat brain. Immunoblots were carried out with anti-tau antibodies 134 and AT8. Lanes: 1, tau24; 2, tau24+brain extract; 3, tau24 S199A; 4, tau24 S199A +brain extract; 5, tau24 S202A; 6, tau24 S202A +brain extract; 7, tau24 S199A, S202A; 8, tau24 S199A, S202A+brain extract.

EXAMPLE I

Preparation of the Monoclonal antibodies AT8 (IgG1, λ)

1. Preparation of the antigen for immunization:

Postmortem tissue, consisting mostly of gray matter from the frontal and temporal cortex, was obtained from histologically confirmed Alzheimer patients. This Alzheimer gray matter brain sample (5–10 g) was homogenized with 10 vol. of cold buffer H (10 mM Tris/1 mM EGTA/0.8 M NaCl/10% sucrose, pH 7.4) in a Teflon/glass Potter S (Braun, Germany) homogenizer. After centrifugation in a 60 Ti MSE rotor at 27,000×g for 20 min at 4° C., the pellet was removed and the supernatant was adjusted to 1 (wt/vol) N-laurosylsarcosine and 1% (vol/vol) 2-mercaptoethanol and incubated while rotating on a mixer 820 (Swelab, Sweden) for 2,5 hours at 37° C. The supernatant mixture was centrifuged at 108,000×g for 35 min at 20° C. The PHF-tau containing pellet was gently washed with PBS and finally suspended in 1 ml of the same buffer.

The antigen preparation was evaluated by a 10% sodium dodecyl sulfate-polyacrylamide gel electrophoresis and followed by Western blotting using immunoblotting with polyclonal rabbit antihuman normal tau antiserum.

2. Immunization protocol and fusion procedure:

Balb/c mice were primed with 100 µg partially purified PHF-tau in complete Freund's adjuvant and boosted three times thereafter at 3-week intervals with 100 µg of the same antigen in incomplete Freund's. On days 3 and 2 before the fusion, mice were boosted with 100 µg PHF-tau saline.

Mouse spleen cells were fused with SP2/0 cells, using a modified procedure of Köhler and Milstein (Köhler, G. and Milstein, C., 1975), with PEG 4000.

Half of the cells were suspended at a density of 4.5×10⁴ spleen cells/well on thirty 96-well peritoneal macrophage feeder layer plates. These wells were screened after 12 days for anti-tau antibody production in a sandwich ELISA either specific for normal tau or for PHF-tau. The other half of the fusion was grown for three days in tissue culture flasks and stored frozen in liquid nitrogen. Hybridoma growth was selected by Dulbecco's modified Eagle's medium (DMEM) supplemented with 20% fetal calf serum, sodium pyruvate (1 mM), L-glutamine (2 mM), penicillin (100 U/ml), streptomycin (100 mg/ml), and nonessential amino acids. All products were purchased from Gibco, Paisley, U.K. Cells were incubated in a humidified 8% $CO_2$ air incubator.

3. Sandwich ELISA for antibody screening:

The screening ELISA used for the detection of anti-tau monoclonal antibodies was a sandwich ELISA system with polyclonal rabbit anti-human tau antibodies in the coating phase. For this purpose polyclonal rabbit anti-human tau serum was affinity-purified (as described in the passage hereinafter entitled "Production of polyclonal rabbit anti-tau antiserum" in Example IV). Purified human normal tau (prepared as described in the passage hereinafter entitled "Production of affinity purified human tau" in Example IV) was used for the preparation of an immuno-affinity column using cyanogen bromide-activated Sepharose (Pharmacia, LKB Sweden). The affinity-bound anti-tau fraction was eluted from this column with a citric acid buffered solution at pH 2.5. After neutralization, the anti-tau-containing fractions were pooled and coated overnight (1 μg/ml) at 4° C. on high-binding microtiter plates (Nunc, Gibco, Paisley, UK) in coating buffer (10 mM Tris, 10 mM NaCl, 10 mM NaN$_3$, pH 8.5). After overcoating for 30 min with 125 μl 10%-saturated casein in PBS to reduce nonspecific binding, the plates were incubated with 100 μl of an appropriately diluted PHF-tau preparation and incubated for 60 min at 37° C. The plates were washed three times with PBS-0.05% Tween 20 (v/v); 100 μl hybridoma supernatant was added, and incubation was continued for 1 h at 37° C. After washing, the bound monoclonal antibodies were detected with peroxidase-conjugated rabbit anti-mouse serum (Dakopatts, Glostrup, Denmark). All reagents were diluted in PBS with 10% casein. After final washing, 100 μl 0.42 mM 3,5,3',5'-tetramethylbenzidine, 0.003% H$_2$O$_2$ v/v in 100 mM citric acid, 100 mM disodium hydrogen phosphate, pH 4.3, was added as peroxidase substrate. The reaction was stopped with 50 μl of a 2 M H$_2$SO$_4$ solution.

Absorbance was read in a Titertek Multiscan (Flow Laboratories, Eflab, Oy, Finland) at 450 nm.

The cross-reactivity of the monoclonal antibodies with normal tau in ELISA was tested in a sandwich ELISA identical to the screening assay, except that affinity-purified normal tau was used instead of PHF-tau. The hybridoma-secreting antibodies specifically recognizing the PHF-tau was subcloned by limiting dilutions. Said hybridoma which secretes the AT5 antibodies will be designated AT5.

EXAMPLE II

Detection of Pathological Tau and Absence of Detection of Normal Tau in ELISA by Western Blotting 1. Detection of abnormally phosphorylated tau in ELISA and absence of detection of normal tau in ELISA:

According to the protocol outlined in Example I, section 3, affinity purified polyclonal anti-tau antibodies were coated on ELISA plates and reacted with different dilutions of either affinity-purified normal tau as described in the passage titled "Production of affinity purified human tau" or of PHF-tau, each prepared in a solution of PBS and 10% casein. After washing, the plates were incubated with a fixed concentration of the ATB monoclonal antibodies. All subsequent procedures were as described (Example I, section 3). The results shown in Table I clearly indicate that the AT8 monoclonal antibodies react only with PHF-tau.

TABLE I

Detection of PHF-tau or normal tau in ELISA using the AT8 monoclonal antibodies for detection

|  | A$_{150}$ nm |
| --- | --- |
| PHF-tau | |
| 1/20 | 1,459 |
| 1/200 | 1,179 |
| 1/2000 | 0,565 |
| Normal tau | |
| 1 μg/ml | 0,021 |
| 100 ng/ml | 0,005 |
| 10 ng/ml | 0,001 |
| Blank | 0,000 |

The assays were performed as outlined in Example I, section 3. Different dilutions of PHF-tau or normal tau were used, as indicated in the table.

The reactivity pattern of the AT8 monoclonal antibodies was also studied in brain homogenates. To this end, high-binding microtiter plates (Nunc, Gibco, Paisley, UK) were coated overnight at 4° C. with 2 μg/ml of purified AT8 monoclonal antibodies in coating buffer (10 mM Tris, 10 mM NaCl, 10 mM NaN$_3$, pH 8.5).

Overcoating to reduce non-specific binding was performed for 30 min with 120 μl blot buffer (5%, w/v skimmed dried milk and 10% v/v newborn calf serum). After washing 3 times with PBS-0.05% Tween 20 (v/v), 100 μl sample was added, and the incubation was carried out for 1 h at 37° C. The plates were washed again three times and incubated with 100 μl of a 1/2000 dilution of rabbit anti-tau serum. Next, the plates were washed again three times, after which 100 μl horseradish peroxidase conjugated donkey anti-rabbit serum diluted 1/2000 in blot buffer was added and the incubation was continued for 30 min. The plates were washed and 100 μl of a solution consisting of 0.42 mM 3,5,3',5'-tetramethylbenzidine, 0.003% H$_2$O$_2$ v/v in 100 mM citric acid, 100 mM disodium hydrogen phosphate, pH 4.3 was added as substrate. The reaction was stopped with 50 μl of a 2 M H$_2$SO$_4$ solution. Absorbance was read in Titertek Multiscan (Flow Laboratories, Eflab, Oy, Finland) at 450 nm.

As can be seen from FIG. 1, the brain homogenates of the 4 Alzheimer patients (AD$_1$–AD$_4$) reacted positively at two different dilutions, while all extracts prepared from brain derived from patients who died of non-neurological diseases (C$_1$–C$_4$) were clearly negative at both dilutions.

2. Detection of pathological tau in Western blotting and absence of detection of normal tau in Western blotting:

Purified normal human tau and PHF-tau were applied to 10% SDS-polyacrylamide gels and run under denaturing conditions according to Laemmli (1970).

After SDS-PAGE, the transfer to nitrocellulose (Hybond-C, Amersham, Brussels, Belgium) was carried out in 10 mM NaHC$_3$, 3 mM Na$_2$CO$_3$, pH 9.9 for 120 min at 55 V with cooling. After blotting, the nitrocellulose was equilibrated to phosphate buffered saline (PBS), and protein binding sites were blocked with blot buffer (PBS supplemented with 5% w/v skimmed dried milk and 10% v/v newborn calf serum). Blotted proteins were incubated overnight at 4° C. with AT8 as primary antibody. After three washings with PBS-0.05% Tween 20 (v/v), horseradish peroxidase-labeled rabbit anti-mouse immunoglobulins (Dakopatts, Glostrup, Denmark) were used at a dilution of 1/3000 and were incubated for 90 min at room temperature. All antisera were diluted in blot buffer. The blots were then washed three times in PBS/Tween and developed with substrate solution (PBS, 0.05% w/v 3,3'-diaminobenzidine, 0.03% v/v H$_2$O$_2$) after which the reaction was stopped in H$_2$O. Results, shown in FIG. 2 indicate that the AT8 antibody recognizes 64 and 68 kDa tau isoforms but show that normal tau bands remain unstained.

EXAMPLE III

Detection of Tau by Immunocytochemistry

Paraffin sections of formalin-fixed brain tissue from neocortex, hippocampus, cerebellum, pons and spinal cord of several Alzheimer patients and age-matched controls were prepared, as well as sections of peripheral nerve from one control patient.

Cryostat sections from Alzheimer and age-matched control brain were also prepared. Tissues were immunostained either with the peroxidase-antiperoxidase (PAP) technique (Steinberger, L. A. et al., 1970) or with the avidin-biotin complex (ABC) technique (Hsu, S. M. et al., 1981) using Dakopatts (Denmark) and Amersham (UK) reagents, respectively. Briefly, after blocking nonspecific interactions with normal swine serum (Dakopatts X901) diluted 1:25 in Tris-buffered saline (TBS) containing 1% bovine serum albumin (BSA), sections were incubated overnight with the AT8 primary antibody appropriately diluted in TBS/BSA. Secondary antibody and peroxidase complex were then applied for 30 min each, with intermediate rinsing in TBS. Color was developed with 3,3'-diaminobenzidine tetrahydrochloride (Sigma). Sections were counterstained with Harris' hematoxylin, dehydrated, coverslipped, and viewed under a light microscope.

FIG. 3 (A to D) clearly indicates that AT8 does not decorate any normal structures but only produces abundant staining of NFT, dystrophic neurites in plaques, and dispersed staining of neuropil (neuropil threads). Some apparently tangle-free neurons were diffusely stained, often exhibiting a strong perinuclear staining.

EXAMPLE IV

Competition ELISAs to Characterize the Epitopes of Known Antibodies with the Antibody of the Invention Affinity-purified rabbit anti-human tau polyclonal antibody was coated overnight at 4° C. in the wells. Plates were washed, and 100 μl of purified abnormally phosphorylated tau, mixed with affinity-purified normal tau, was added per well for 1 h at 37° C. After washing, 50 μl of the different unlabeled monoclonal antibodies to be tested were added in several dilutions. Subsequently, 50 μl biotinylated AT8 antibody or biotinylated BT2 antibody obtained as described in the passage titled "Production of the monoclonal antibody BT2" was added in an amount previously determined to provoke 50% of the maximal binding. After 1 h at 37° C. the plates were washed and a streptavidine biotin peroxidase complex was added for 30 min to allow detection of the ELISA with 3,5,3',5'-tetramethylbenzidine. After stopping the reaction with 2 M $H_2SO_4$ the plates were read in a Titertek Multiscan plate reader (Flow) at 450 nm.

As the results of Table II indicate, the BT2 antibodies inhibit the binding of biotinylated BT2, while casein or AT8 do not influence this binding. Conversely, the ATS antibody completely blocks the binding of biotinylated AT8, but neither casein or BT2 inhibit this reaction.

TABLE II

Competition ELISA to characterize the epitopes of known antibodies.

| Concentration | BT2-bio | | | AT8-bio | | |
| --- | --- | --- | --- | --- | --- | --- |
| | Casein | BT2 | AT8 | Casein | BT2 | AT8 |
| 9 μg/ml | 0.369 | 0.071 | 0.369 | 0.578 | 0.548 | 0.056 |
| 3 μg/ml | 0.390 | 0.088 | 0.375 | 0.573 | 0.557 | 0.054 |
| 1 μg/ml | 0.375 | 0.122 | 0.368 | 0.548 | 0.550 | 0.059 |
| 333 ng/ml | 0.381 | 0.179 | 0.369 | 0.564 | 0.556 | 0.093 |
| 111 ng/ml | 0.385 | 0.245 | 0.381 | 0.576 | 0.573 | 0.155 |
| 37 ng/ml | 0.395 | 0.318 | 0.360 | 0.568 | 0.549 | 0.282 |

BT2 or AT8 were used at the indicated concentrations in the left column. All antibody dilutions were carried out in casein which was also used at the same concentration in the casein controls (column marked casein).

Production of polyclonal rabbit anti-tau antiserum:

New Zealand white rabbits were immunized with affinity purified human tau. Rabbits were injected intradermally with 100 μg affinity purified human tau emulsified in complete Freund's adjuvant. Two weeks later, this was repeated intramuscularly with 200 μg affinity purified human tau in incomplete Freund's, and a third intramuscular injection was carried out after one week with 100 μg affinity purified human tau in saline. The rabbits were bled one week after the third injection, evaluated and again injected twice, after a month's interval with the same amount of tau as used for the third injection. The sera were evaluated in a solid phase ELISA with affinity purified human tau in the coating phase and in Western blot against affinity purified human tau.

Production of affinity purified human tau:

Typically, 50 grams post-mortem human brain was out into small pieces with scissors and homogenized 1/1 (W/V) in buffer A (20 mm w (2-(N-morpholino)ethanesulfonic acid), 80 mM NaCl, 2 mM EDTA, 0.1 mM EGTA, 1 mM $MgCl_2$, 1 mM mercaptoethanol, pH 6.75) with a Potter homogenizer equipped with a teflon plunger. The homogenate was centrifuged for 1 h at 150000 g at 4° C., and the supernatant was heated for 5 min in boiling water and chilled again for 10 min on ice. The slurry was centrifuged for 2 h at 150000 g at 4° C., and the supernatant was collected thereafter and called the "heat stable cytosolic extract".

Ten mg BT2 anti-tau monoclonal antibody, purified from ascites fluid on protein G (Pharmacia, Uppsala, Sweden), was coupled to 1 gram cyanogen-bromide activated by Sepharose (Pharmacia) following the method proposed by the manufacturer. Fifty ml of the heat-stable cytosolic extract were diluted ½ in 0.1 M phosphate buffer pH 8.5 and applied to the column. The column was washed with 0.1 M phosphate and tau was eluted with 0.1 M citric acid pH 2.5 and neutralized immediately with 1 M NaOH. Fractions were evaluated in 10% SDS-PAGE in immunoblotting with anti-tau antibodies.

Production of the monoclonal antibody BT2:

Antigen purification:

Bovine tau: tau was purified from bovine brain by a modification of the perchloric acid method of Lindwall et al. (1984). Typically, 50 grams fresh brain was cut into small pieces with scissors and homogenized 1/1 (w/v) in buffer A (20 mM w(2-(N-morpholino)ethanesulfonic acid), 80 μM NaCl, 2 mM EDTA, 0.1 M EGTA, 1 MM $MgCl_2$, 1 mM mercaptoethanol, pH 6.75) with a Potter homogenizer equipped with a teflon plunger. The homogenate was centrifuged for 1 h at 150000 g at 4° C., and the supernatant was heated for 5 min in boiling water and chilled again for 10 min on ice. The slurry was centrifuged for 2 h at 150000 g at 4° C., and the supernatant was collected thereafter. The heat stable cytosolic extract was made to 2.5% perchloric acid and was centrifuged for 1 h at 150000 g at 4° C. after which the supernatant was neutralized with 3 M Tris. The supernatant was then dialyzed and concentrated in water in a centriprep concentrater (Amicon, Lausanne, Switzerland). The end product, hereinafter referred to as the "bovine tau", was evaluated in sodium dodecyl sulfate-polyacrylamide gel electrophoresis (SDS-PAGE) performed according to the method of Laemmli (1970).

Monoclonal anti-bovine tau antibody production:

Balb/c mice were primed with 100 μg purified bovine tau in complete Freund's adjuvant and boosted 3 times with 100 μg bovine tau in complete Freund's every two weeks. On days 3 and 2 before the fusion, the mice were boosted again with 100 μg bovine tau in saline. SP2/0 myeloma cells were used as fusion partner, and the fused cells were seeded on mouse peritoneal macrophage feeder cells. Half the hybridomas were seeded in 96-well places and screened after 10 days in a solid-phase ELISA on bovine tau for anti-tau antibody production, the other half of the fusion was grown for one day in tissue flasks, and these cells were frozen and stored in liquid nitrogen. All hybridomas were grown in Dulbecco's modified Eagle's medium (DMEM) supplemented wioth 10% fetal calf serum, sodium pyruvate (1 mM), L-glutamine (2 mM), penicillin (100 U/ml), streptomycin (100 µg/ml), and nonessential amino acids. All products were purchased from Gibco, Paisley, U. K. Cells were incubated at 37° C. in a humidifed 8% $CO_2$ air incubator. Positive signals in ELISA were tested in Western blot against heat stable cytosolic extract from bovine brain with the anti-tau antibody tau-2 (Sigma, St. Louis, Mo.) as a control. Positive wells were subcloned and the clones were frozen in liquid nitrogen.

EXAMPLE V

Expression and Phosphorylation of Mutant Recombinant Tau Proteins to Determine the Essential Phosphorylation Site(s) of the AT8 Epitome A full-length cDNA clone (htau24), corresponding to a four repeat isoform of tau and with a NdeI site in the context of the initiator codon, was subcloned into the EcoRI site of M13mp18. Two constructs were made in which site-directed mutagenesis was used to change codon 199 (S to A) or codon 202 (S to A) (using the numbering of the longest human brain tau isoforms (Goedert, M. et al., 1989), and a third construct was made, where codons 199 and 202 were both changed to A. Following cleavage with NdeI and EcoRI, the resulting fragments were subcloned downstream of the T7 RNA polymerase promoter in the expression plasmid pRK172, and the recombinant plasmids were transformed into *E.coli* BL21 (DE3) cells. The bacterial cultures were grown, induced and harvested as desribed (Goedert, M. et al., 1989).

The pellet from a 500 ml culture was resuspended in 20 ml of extraction buffer (50 mM PIPES, pH 6.8, 1 mM DTT, 1 mM EDTA, 0.2 mM PMSF, 0.5 µg/ml leupeptin, 0.5 µg/ml pepstatin) and sonicated for 2×3 min using a Kontes microultrasonic cell disrupter. Following centrifugation (15,000 rpm for 15 min), the supernatant was passed through a DE-52 cellulose column. The flow-through was loaded onto a phosphocellulose column (bed volume 3 ml) equilibrated in the extraction buffer. After exhaustive washing with the extraction buffer, protein was eluted batchwise with 3 ml aliquots of extraction buffer containing 0.5 M NaCl. The fractions containing the recombinant tau isoforms were pooled and dialyzed overnight against 50 mM MES, 1 mM DTT, pH 6.25. After centrifugation, the dialysate was loaded onto a fast flow carboxymethyl-Sepharose HR 5/5 column. The column was washed with 50 mM MES, 1 mM DTT, 50 mM NaCl, pH 6.25, and the protein was eluted using 100–300 mM NaCl in 50 mM MES, 1 mM DTT, pH 6.25, gradient. Column fractions were screened by gel electrophorisis, and the peak tau fractions were pooled and dialyzed against 40 mM HEPES, 1 mM DTT, 0.2 mM PMSF, pH 7.2. The protein concentrations were determined by amino acid composition.

The resulting recombinant tau proteins were phosphorylated, using brain protein kinase activity as follows:

Adult rat brain was homogenized (1 g/2.5 ml) in 10 mM Tris/HCl, pH7.4, 5 µm EGTA, 2 mM DTT, 1 µM okadaic acid, 1 mM PMSF, 20 µg/ml leupeptin, 20 µg/ml aprotinin and 20 µg/ml pepstatin and centrifuged at 40,000 rpm for 1 h at 4° C. The supernatant was used directly for phosphorylation. Incubations were carried out at 37° C. with 40 mM HEPES, pH 7.2, 2 mM AtP, 2 mM $MgCl_2$, recombinant tau protein (1 µM), and rat brain extract (0.05 ml) for 24 h, and aliquots were then taken for immunoblotting. Controls were incubated under the same conditions, except that the brain extract was omitted.

The AT8 epitope of the phosphorylated recombinant tau proteins was analyzed by immunoblots. SDS-PAGE was carried out using 10% or 10–20% gradient minigels. For immunoblotting, phosphorylated and non-phosphorylated recombinant tau proteins were transferred to a polyvinylidene difluoride (PVDF) membrane, and residual protein binding sites were blocked with 1% gelatin in phosphate-buffered saline. The blots were then incubated for 5 h at room temperature with anti-tau antiserum 134 (dilution 1:250) (Goedert, M. et al., 1989) or with antibody AT8 (dilution 1:500). Bound antibody was detected by the biotin/peroxidase system (Vectastain).

The results of the immunoblots show that phosphorylation of at least the Ser 202 of the AT8 epitope is required for antibody recognition.

REFERENCES

1. Baudier, J. and Cole, R. D., J. Biol. Chem. 262, 17577–17583.

2. Binder, L. I., Frankfurter, A. and Rebhun, L. I., J. Cell Biol. 101, 1371–1378 (1985).

3. Bre, M. N. and Karsenti., E., Cell Motil. Cytoskeleton 15, 88–98 (1990).

4. Brion, J. P., Couck, A. M., Passareiro, H. and Flament-Durand, J., J. Submicrosc. Cytol., 17, 89–96 (1985).

5. De Bont, H. B. A., Van Boom, J. H. and Liskamp, R. M. J., Tetrahedron Lett. 31, 2497–2500 (1990).

6. Delacourte, A., Flament, S., Dibe, E. M., Hublau, P., Sablonniere, B., Himon, B., Sherrer, V. and Defossez, A., Acta Neuropathol. 80, 111–117 (1990).

7. Flament, S., Delacourte, A., Hemon, B. and Defossez, A., J. Neurol. Sci. 92, 133–141 (1989).

8. Flament, S., Delacourte, A. and Mann, D. M. A., Brain Res. 516, 15–19 (1990).

9. Flament, S. and Delacourte, A., Nature 346, 6279 (1990).

10. Ghanbari, H. A., Kozuk, T., Miller, B. E. and Riesing, S., J. Clin. Laboratory Anal. 4, 189–192 (1990).

11. Goedert, M., Spillantini, M. G., Jakes, R., Rutherford, D. and Crowther, R.-A., Neuron 3, 519–526 (1989).

12. Goedert, M., Spillantini, M. G. and Jakes, R., Neurosci. Lett., 126, 149–154 (1991).

13. Greenberg, S. G. and Davies, P., Proc. Natl. Acad. Sci. U.S.A., 87, 5827–5831 (1990).

14. Harrington, C. R., Edwards, P. C. and Wischik. C. M., J. Immunol. Methods 134, 261–271 (1990).

15. Himmler, A., Mol. Cell. Biol., 9, 1389–1396 (1989).

16. Hsu, S. M., Raine, L. and Faer. H., J. Histochem. Cytochem. 29, 577–580 (1981).

17. Iqbal, K., Zaidi, T., Thompson, C. H., Merz, P. A. and Wisniewski, H. M., Acta Neuropathol. 62, 167–177 (1984).

18. Ishiguro, K., Y. Ihara, T. Uchida and K. Imahori, J. Biochem. 104, 319–321 (1988).

19. Kosik, K. S., Orecchio, L. D., Binder, L., Trojanowski, J. Q., Lee, V. M. Y. and Lee, G., Neuron., 1, 817–825 (1988).

20. Kosik, K. S., Crandall, J. E., Mufson, E. and Neve, R. L., Ann. Neurol. 26, 352–361 (1989).

21. Ksiezak-Reding, H., Dickson, D. W., Davies, P. and Yen, S. H., Proc. Natl. Acad. Sci. U.S.A., 84, 3410–3414 (1987).

22. Ksiezak-Reding, H., Davies, P. and Yen, S. H., J. Biol. Chem., 263, 7943–7947 (1988).

23. Ksiezak-Reding, H., Chien, C. H., Lee, V. M. Y. and Yen, S. H., J. Neurosci. Res., 25, 412–419 (1990).

24. Köhler, G. and Milstein, C., Nature, 256, 495–497 (1975).

25. Laemmli, U. K. Nature 227, 680–685 (1970).

26. Lee, G., Cowan, N. and Kirschner, M., Science, 239, 285–288 (1988).

27. Lee, V. M. Y., Balin, B. J., Otvos, L. and Trojanowski, J. Q., Science, 251, 675–678 (1991).

28. Mehta, P. D., Thal, L., Wisniewski, H. M., Grundke-Iqbal, I. and Iqbal, K., The Lancet, July, 35- (1985).

29. Mercken, M., Vandermeeren, M., Lübke, U., Six, J. Boons, J., Vanmechelen, E., Van de Voorde A. and Gheuens, J., J. Neurochem., in press.

30. Nukina, N., Kosik K. S. and Selkoe, D. J., Proc. Natl. Acad. Sci. U.S.A. 84, 3415–3419 (1987).

31. Nukina, N., Kosik K. S. and Selkoe, D. J., Neurosci. Lett 87, 240–246 (1988).

32. Perry, G., Mulvihill, P., Fried, V. A., Smith, H. T., Grundke-Igbal, I. and Iqbal, K., J. Neurochem. 52, 1523–1528 (1989).

33. Steinberger, L. A., Hardy, P. R., Cuculis, J. J. and Meyer, H. G., J. Histochem. Cytochem. 18, 315–333 (1970).

34. Steiner, B., Mandelkow, E. M., Biernat, J., Gustke, N., Meyer, H. E., Schmidt, B., Mieskes, G., Soling, H. D., Drechsel, D., Kirschner, M. W., Goedert, M. and Mandelkow, E., The EMBO Journal 9, 3539–3544 (1990).

35. Towbin, H., Staehelin, T. and Gordon, J., Proc. Natl. Acad. Sci. U.S.A. 76, 4350–4354 (1979).

36. Vallee, R. B., J. Cell Biol., 92, 435–442 (1986).

37. Weingarten, M. D., Lockwood, A. H., Hwo, S. Y. and Kirschner, M. W., Proc. Natl. Acad. Sci. U.S.A. 72, 1868–1862 (1975).

38. Wischik, C. M., Novak, M., Edwards, P. C., Klug, A., Tichelaar, W. and Crowther, R. A., Proc. Natl. Acad. Sci. U.S.A., 85, 4884–4888 (1988).

39. Wisniewski, H. M., Mehta, P. D., Kim, K. S. and Merz, G. S., Biological Markers of Alzheimer's Disease., Boller, Katzman, Rascol, Signoret & Christian eds., 23–29 (1989).

40. Wolozin, B. and Davies, P., Ann. Neurol. 22, 521–526 (1987).

41. Wolozin, B. L., Pruchnicki, A., Dickson, D. W. and Davies, P., Science 232, 648–650 (1986).

42. Lindwall, G. and Cole, R. D. (1984). The purification of tau protein and the occurrence of two phosphorylation states of tau in brain. J. Biol. Chem. 259, 12241–12245.

What is claimed is:

1. A monoclonal antibody secreted by the hybridoma deposited at ECACC on Oct. 08, 1991 under No. 91100806.

2. A hybridoma, which secretes a monoclonal antibody according to claim 1.

3. A process for producing monoclonal antibodies comprising the steps of:
    culturing the selected hybridomas according to claim 2, in an appropriate medium culture; and
    recovering the monoclonal antibodies excreted by said selected hybridomas; or alternatively:
    implanting the selected hybridomas of claim 2 into the peritoneum of a mouse and, when ascites has been produced by the animal, recovering the monoclonal antibodies then formed from said ascites.

* * * * *

UNITED STATES PATENT AND TRADEMARK OFFICE
CERTIFICATE OF CORRECTION

PATENT NO. : 6,238,892 B1　　　　　　　　　　　　　　　　　　Page 1 of 2
DATED : May 29, 2001
INVENTOR(S) : Mercken et al.

It is certified that error appears in the above-identified patent and that said Letters Patent is hereby corrected as shown below:

<u>Title page,</u>
Item [57], ABSTRACT,
Line 4, "ca" should read -- can --

<u>Column 4,</u>
Lines 50 and 57, "YSSPGSPGT or YSSPGSPGT" should read
-- YSS*PGS*PGT or YSSPGS*PGT --
Line 51, "YSSPGAPGT" should read -- YSSPGS*PGT --
Line 58, "YSSPGSPGT" should read -- YSSPGS*PGT --

<u>Column 6,</u>
Lines 28-30, "YSSPGSPGT (SEQ ID NO: 1), or YSSPGSPGT (SEQ ID NO: 1)" should read -- YSS*PGS*PGT (SEQ ID NO: 1), or YSSPGS*PGT (SEQ ID NO: 2) --

Lines 36-37 and 40-41, "YSSPGSPGT (SEQ ID NO: 1) or YSSPGSPGT (SEQ ID NO: 1) should read -- YSS*PGS*PGT (SEQ ID NO: 1), or YSSPGS*PGT (SEQ ID NO: 2) --

Line 46, delete "(SEQ ID NO: 2)"
Line 49, "$(X_1)_p(X_2)_q SPX_3 SP(X_4)_r(X_5)_s$" should read --$(X_1)_p(X_2)_q S*PX_3 S*P(X_4)_r(X_5)_s$ --
Line 50, "$(X_1)_p(X_2)_q SPX_3 SP(X_4)_r(X_5)_s$" should read --$(X_1)_p(X_2)_q SPX_3 S*P(X_4)_r(X_5)_s$ --
Line 51, "$(X_1)_p(X_2)_P SPX_3 SP(X_4)_r(X_5)_s$" should read --$(X_1)_p(X_2)_q SPX_3 S*P(X_4)_r(X_5)_s$ --

<u>Column 7,</u>
Line 6, "order,." should read -- order, --

<u>Column 8,</u>
Lines 62-63, "YSSPGSPGT (SEQ ID NO: 1), or YSSPGSPGT" should read
-- YSS*PGS*PGT (SEQ ID NO:1), or YSSPGS*PGT --

<u>Column 11,</u>
Line 44, "ATB" should read -- AT8 --

<u>Column 13,</u>
Line 43, "ATS" should read -- AT8 --

<u>Column 14,</u>
Line 15, "20 mm" should read -- 20 mM --
Line 42, "1MM MgCl$_2$" should read -- 1 mM MgCl$_2$ --

UNITED STATES PATENT AND TRADEMARK OFFICE
CERTIFICATE OF CORRECTION

PATENT NO. : 6,238,892 B1
DATED : May 29, 2001
INVENTOR(S) : Mercken et al.

It is certified that error appears in the above-identified patent and that said Letters Patent is hereby corrected as shown below:

Column 15,
Line 5, "wioth" should read -- with --
Line 21, "epitome" should read -- epitope --

Signed and Sealed this

Eighteenth Day of June, 2002

Attest:

JAMES E. ROGAN
Attesting Officer      Director of the United States Patent and Trademark Office